United States Patent [19]

Shin et al.

[11] Patent Number: 5,418,211
[45] Date of Patent: May 23, 1995

[54] METHODS OF REGULATING PLANT GROWTH WITH POLYHYDRIC ALCOHOLS

[75] Inventors: Charles C. Shin; Nicolai A. Favstritsky; Brent M. Sanders, all of Lafayette, Ind.

[73] Assignee: Great Lakes Chemical Corporation, West Lafayette, Ind.

[21] Appl. No.: 230,609

[22] Filed: Apr. 21, 1994

[51] Int. Cl.6 ..................... A01N 31/02; A01N 43/16
[52] U.S. Cl. ................................ 504/174; 504/176; 504/292; 504/353
[58] Field of Search ................ 504/174, 176, 292, 353

[56] References Cited

U.S. PATENT DOCUMENTS

| | | | |
|---|---|---|---|
| 4,047,925 | 9/1977 | Barer | 71/78 |
| 4,291,497 | 9/1981 | Manankov | 47/58 |
| 4,604,129 | 8/1986 | Schott et al. | 71/76 |
| 5,163,992 | 11/1992 | Rentzea et al. | 71/88 |

*Primary Examiner*—S. Mark Clardy
*Attorney, Agent, or Firm*—Woodard, Emhardt, Naughton, Moriarty & McNett

[57] ABSTRACT

Osmo-adjusting solutes, particularly polyols and/or monosaccharides, are used to control the growth of plants. In particular, aqueous solutions of sorbitol or xylitol are used to reduce plant height and increase stem diameter. The solutions preferably include between about 0.05 and about 25 weight percent of the osmo-adjusting solute, and are applied to the root zone by drenching regularly or prior to transplanting. The solutions are also shown to be effective for conditioning plants for hardiness against certain environmental and handling stresses.

16 Claims, No Drawings

METHODS OF REGULATING PLANT GROWTH WITH POLYHYDRIC ALCOHOLS

BACKGROUND OF THE INVENTION

1. Field of the Invention

The present invention relates generally to compositions and methods for regulating the growth of plants, and more particularly to compositions and methods for producing uniformly stocky plants.

2. Background of the Invention

Transplants have long been used in the vegetable industry to help schedule production, extend the producing season, and gain the advantage of higher prices available to sellers at earlier markets. Further, with some crops it is necessary to use transplants because seed germination cannot effectively be accomplished under cold or otherwise harsh field conditions. Accordingly, the transplant industry is rapidly expanding to meet increased market demand driven by new production technology, high seed costs and the need to reduce production risk.

Vegetable transplants often require treatment to slow their growth. Weather conditions or other factors may dictate a schedule change, or growth reduction may be necessary when transplants are produced under cloudy or high temperature conditions which cause undesirably spindly plants. Short and stocky transplants are easier to ship and handle during the transplanting operation and they better withstand transplant stress. Likewise, as automatic transplanters are developed, the demand for very uniform plants will be greater to allow the automatic planters to operate most efficiently.

It is known that plant growth is regulated by chemical substances, particularly plant hormones, produced within the plant. These plant hormones are organic compounds produced by the plant and active in small amounts which are transported through the plant body influencing growth or other physiological processes. Unlike enzymes, hormones are consumed during metabolic processes and must be renewed if their effects are to continue.

Traditionally, commercial plant regulators have been formulations or synthetic analogs of the following major plant hormone classes: Auxins, Cytokins, Ethylene generators, and Gibbrellins. Occasionally, other hormones have been used.

Plant growth is also regulated by environmental factors, such as changes in water potential and temperature. For example, when a plant is exposed to water stress (drought, cold and salt stress), water potential decreases as does the cellular growth of the plant. Decreasing external water potential by −0.1 Mpa (sometimes less) results in a perceptible decrease in cellular growth.

Due to recent restrictions on the use of chemical plant growth regulators, the development of alternative methods of practical growth control and conditioning of transplants has been increasingly studied. In this regard, growers are using water/fertilizer restriction, temperature regulation, and mechanical brushing to attempt to achieve desired growth regulation results. None of these prior art methods, however, has provided the desired results in an economically advantageous manner.

A need therefore exists for plant growth regulations which are non-toxic to the plants, environmentally acceptable and relatively inexpensive. The present invention addresses that need by providing compositions and methods which reduce plant growth and condition the plants for hardiness against environmental and handling stresses.

SUMMARY OF THE INVENTION

Briefly describing one aspect of the present invention, there is provided a method for reducing plant growth, comprising a method for reducing plant growth, comprising applying to the plant a growth reducingly effective amount of a growth reducing composition selected from the group consisting of polyols of the formula

where n=0 to 4, and monosaccharides of the formula $(CH_2O)_n$ where n=3 to 6, and mixtures thereof. The solution is applied to the root zone by drenching regularly or prior to transplanting. The solution preferably includes between about 0.05 and about 25 weight percent of the growth reducing and conditioning agent. The inventive plant growth regulators are also shown to be effective for conditioning plants for hardiness against certain environmental and handling stresses.

One object of the present invention is to provide compositions and methods for reducing the growth of plants.

Another object of the present invention is to provide compositions and methods for conditioning plants for hardiness against certain environmental and handling stresses, e.g. those which occur in conjunction with transplanting, excessive cold, drought, water deficits, and excessive salt concentration in soil media.

A further object of this invention is to provide plant growth regulating and conditioning compositions and methods which are relatively inexpensive, non-toxic and environmentally acceptable.

Further objects of the present invention will be apparent from the following description.

DESCRIPTION OF THE PREFERRED EMBODIMENT

For the purposes of promoting an understanding of the principles of the invention, reference will now be made to preferred embodiments and specific language will be used to describe same. It will nevertheless be understood that modifications and further applications of the principles of the invention are contemplated as would normally occur to one skilled in the art to which the invention relates.

In accordance with this invention, novel plant growth reducing and conditioning agents have been discovered comprising an aqueous solution containing a plant growth reducing and conditioning component selected from the group consisting of osmo-adjusting solutes, their analogs, and mixtures thereof. Preferably, the composition comprises an aqueous solution comprising between about 0.05 and about 25 weight percent of the growth reducing component, and most preferably comprises between about 0.5 to 10 weight percent of the growth reducing component. It has also been discovered that the growth reducing composition is effective in conditioning the plant tissue for hardiness against environmental and handling stresses.

As used hereinafter, osmo-adjusting solutes are organic compounds that may be used to reduce the water potential of plant tissue. Osmo-adjusting compounds include glycerol, sorbitol, xylitol, mannitol, arabitol, proline, aspartic acid, glutamic acid, betaine (glycinebetaine), and alaninebetaine.

All osmo-adjusting solutes and their analogs are acceptable for use in the present invention. Preferred osmo-adjusting solutes are polyols of the formula $$CH_2OH(CHOH)_nCH_2OH$$

where n=0 to 4. Also preferred are monosaccharides of the formula $$(CH_2O)_n$$

where n=3 to 6. Sorbitol and xylitol are most preferred for use in the present invention.

Sorbitol may be obtained from berries, cherries, plums, pears, apples, seaweeds or algae according to known techniques. It is prepared industrially from glucose by high pressure hydrogenation or by electrolytic reduction, and is available to one of ordinary skill in the art without undue experimentation.

Xylitol is found as a natural intermediate in the metabolism of D-glucose through glucuronate cycle in livers. It is generally prepared by the reduction of xylose, and is used as oral and intravenous nutrient and in anticaries preparations. Xylitol has an $LD_{50}$ in mice of approximately 22 gram/kilogram, and is available to one of ordinary skill in the art without undue experimentation.

Plant growth may be retarded by applying the growth reducing compositions of the present invention by methods such as root drenching or drip irrigation. Alternatively, roots may be soaked directly in the growth reducing composition. Any conventional apparatus suitable for root drenching may be employed. Depending on the degree of growth reduction and conditioning desired, repeat applications may be appropriate. Second and subsequent applications are generally applied after intervals of up to one week.

Maximum growth differences between treated and non-treated plants are achieved about one week after application of the composition. The degree of growth reduction is a function of the degree of osmo-adjustment, which is a function of outside water stress caused by the concentration of the inventive compositions.

The compositions may be formulated and supplied to the user at the desired strength or in concentrated form and diluted to the desired strength prior to application to the plants. No special handling and mixing steps are required. However, since the active ingredient is a carbohydrate, prolonged storage should be avoided after the composition is formulated.

Although plants respond immediately to the treatment of the present invention, it is preferred for some applications that the compositions include non-ionic surfactants. Suitable surfactants operate as penetrating agents and otherwise may be inert, or at least non-interfering, components. For example, two different surfactants, polyoxyethylene sorbitan monolaurate (Tween 20) and polyoxyglycol siloxane (Silwet 77) have been found to accelerate the effectiveness of the compositions in appropriate circumstances. When non-ionic surfactants are used, it is preferred that the composition contain between about 0.005 and about 0.5 weight percent of the non-ionic surfactant.

As indicated, the growth reducing methods of the present invention are applicable for the treatment of plants desired to be reduced and conditioned for hardiness against a variety of environmental and handling stresses. These forms of stress are related by the fact that the stresses are manifest as water-related effects. Accordingly, the inventive methods may further be applicable to a wide range of environmental and handling stresses, as well as to many types of plants and plant products.

The following examples will further illustrate the invention, with all percentages being by weight unless otherwise indicated. It will be appreciated that these examples are demonstrative only, and the applicability of the methods described herein extends to various other plants and plant products, as well as differing types of environmental and handling stresses.

EXAMPLE 1

The efficacy of the present invention is demonstrated by results showing reduction in plant heights induced by the application of osmo-adjusting compositions. A set of 15 tomato plants (c.v. IPB) with similar growth development was selected. The average height of the plants was 3.5 cm. The plants were divided into three sets (five plants per set). For each treatment, the first set was root drenched with DI water, the second set was root drenched with an aqueous solution of 5% sorbitol. Plant heights and stem diameter were measured five days, ten days, and 15 days after the treatment as shown in Table 1.

The results indicate that plants treated with aqueous solutions of 2.5% or 5% sorbitol were shorter and stockier than the control plants. In particular, treated plants were reduced in height by 20% and 35%, respectively, compared with controls. The decrease in the ratio between plant height and stem diameter shows that the stem is relatively thicker for the treated plants than the control plants. It was also observed that plants treated with the present invention were greener than the control plants.

TABLE 1

| Average Growth Developments per Five Tomato Plants | | | | |
|---|---|---|---|---|
| Days After Drench | Treatment | Plant Height (cm) | Stem Diameter (mm) | Ht/SD |
| 0 day* | DI water | 3.50 | 1.70 | 2.06 |
| | 2.5% sorbitol | 3.50 | 1.70 | 2.06 |
| | 5.0% sorbitol | 3.50 | 1.70 | 2.06 |
| 5 days | DI water | 4.70 | 2.30 | 2.04 |
| | 2.5% sorbitol | 4.30 | 2.20 | 1.95 |
| | 5.0% sorbitol | 4.02 | 2.06 | 1.95 |
| 10 days | DI water | 6.70 | 2.97 | 2.26 |
| | 2.5% sorbitol | 5.80 | 2.66 | 2.18 |
| | 5.0% sorbitol | 4.74 | 2.53 | 1.87 |
| 15 days | DI water | 8.00 | 3.27 | 2.45 |
| | 2.5% sorbitol | 6.40 | 2.71 | 2.36 |
| | 5.0% sorbitol | 5.20 | 2.71 | 1.92 |

*average values of all 15 plants immediately prior to treatments

EXAMPLE 2

The experimental procedure of Example 1 was repeated. A set of 15 tomato plants each of three different cultivars was treated in the same way as in Example 1. Plant heights and stem diameters were measured 15 days after treatment. The results (Table 2) show that compositions of the present invention are effective in reducing growth of all three different cultivars of the tomato plants. Tomato plants treated with an aqueous solution of 5% sorbitol are shorter than the control plants by about 35% for IPB, 23.5% for S129, and 30.7% for Allegro 15 days after the treatments. The percent reduction in growth is greater for higher concentration treatments.

TABLE 2

Average Growth Developments per Five Tomato Plants of Three Different Cultivars 15 Days After the Treatment

| Cultivar | Treatment | Plant Height (cm) | Stem Diameter (mm) | Ht/SD |
|---|---|---|---|---|
| IPB | DI water | 8.00 | 3.27 | 2.45 |
| | 2.5% sorbitol | 6.40 | 2.71 | 2.36 |
| | 5.0% sorbitol | 5.20 | 2.71 | 1.92 |
| S129 | DI water | 11.90 | 2.52 | 4.72 |
| | 2.5% sorbitol | 11.70 | 2.70 | 4.33 |
| | 5.0% sorbitol | 9.10 | 1.96 | 4.64 |
| Allegro | DI water | 12.26 | 3.29 | 3.73 |
| | 2.5% sorbitol | 9.80 | 2.47 | 3.97 |
| | 5.0% sorbitol | 8.50 | 2.28 | 3.73 |

EXAMPLE 3

The effectiveness of various osmo-adjusting solutes and their analogs in reducing growth of pepper plants were compared on an equi-molal concentration basis. Two hundred pepper plants were germinated in a seedling tray. The plants were divided into two sets (90 plants per set) by removing two rows (20 plants) from the middle of the tray. One set (90 plants) of each tray was treated with a 0.049 molal aqueous solution of polyethylene glycol (molecular weight 300 and 1500), glycerol, 1,2-propanediol, ascorbic acid, and isoascorbic acid, while the other set was treated with distilled water. The treatments were repeated three times in four day intervals.

Pepper plants treated with compositions of the present invention were significantly shorter than the plants treated with DI water only.

EXAMPLE 4

The experimental procedure in Example 3 was followed. Each one-half tray of tomato plants was treated with aqueous solutions of 0.049 molal polyethylene glycol 300, 1,2-propanediol, ascorbic acid, isoascorbic acid, glycerol and sorbitol. The effectiveness of the treatments on tomato plants was similar to the effectiveness of the treatments on pepper plants in Example 3.

EXAMPLE 5

The general experimental procedure in Example 3 was followed with broccoli. Each one-half tray of broccoli plants was treated with aqueous solutions of various concentrations of sorbitol. Another half tray of broccoli plants was treated with DI water to serve as a control. Plant heights were measured five, 14 and 21 days after the treatments as listed in Table 3. Growth rates in the Table were determined by net growth/number of days for the periods (5–14 and 14–21 days).

The height reducing effect of aqueous solutions of sorbitol on broccoli plants was compared with those of DI water. The broccoli plants treated with sorbitol were significantly shorter than the control plants as on tomato and pepper plants in the previous Examples.

TABLE 3

Growth Developments (Heights) of 23 Day Old* Broccoli Plants Treated With Various Concentrations of Sorbitol

| Treatment | No. of Plants | Plant Height (cm) | | | Growth Rate (mm/day) | |
|---|---|---|---|---|---|---|
| | | 5 | 14 | 21 | 5–14 | 14–21 |
| 0.1 sorbitol | 10 | 10.16 | 12.53 | 17.88 | 2.6 | 7.6 |
| Control | 10 | 10.10 | 14.17 | 17.82 | 4.5 | 5.2 |
| 0.5 sorbitol | 10 | 11.38 | 13.90 | 20.05 | 2.8 | 8.7 |
| Control | 10 | 12.47 | 14.90 | 19.84 | 2.7 | 7.1 |
| 1.0% sorbitol | 10 | 11.09 | 13.62 | 19.89 | 2.8 | 9.0 |
| Control | 10 | 10.78 | 14.55 | 19.51 | 4.2 | 7.1 |
| 2.5% sorbitol | 10 | 10.22 | 12.61 | 16.78 | 2.7 | 6.0 |
| Control | 10 | 12.58 | 16.54 | 20.20 | 4.4 | 5.2 |
| 4.0% sorbitol | 10 | 9.05 | 10.82 | 15.39 | 2.0 | 6.5 |
| Control | 10 | 9.12 | 13.87 | 17.53 | 5.3 | 5.2 |
| 6.0% sorbitol | 10 | 10.65 | 12.93 | 16.55 | 2.5 | 5.2 |
| Control | 10 | 10.94 | 13.40 | 17.81 | 2.7 | 6.3 |
| 8.0% sorbitol | 10 | 10.84 | 14.90 | 13.99 | 4.5 | 0 |
| Control | 10 | 12.07 | 14.50 | 18.02 | 2.7 | 5.0 |
| $LSD_{0.05}$ | | 1.10 | 1.03 | 1.34 | | |

*days old from the sowing date

TABLE 4

Growth Rate of Tomato Plants Treated With Various Concentrations of Sorbitol

| | Growth Rate (mm/day) Age of Plant (days) | | | |
|---|---|---|---|---|
| | 35 | | 41 | |
| | Days After Treatment | | | |
| | 0–6 | 6–12 | 0–6 | 6–12 |
| | No. of Plants/ | | | |
| Treatment | 20 | 20 | 20 | 20 |
| 1% sorbitol | | | 6.4 | 5.1 |
| Control | | | 11.9 | 14.1 |
| % Reduction | | | 46 | 64 |
| 3% sorbitol | 2.7 | 2.5 | 7.8 | 5.1 |
| Control | 4.5 | 3.1 | 11.6 | 10.0 |
| % Reduction | 40 | 19 | 33 | 49 |
| 5% sorbitol | 2.5 | 1.8 | 8.5 | 6.1 |
| Control | 4.1 | 3.1 | 11.8 | 15.6 |
| % Reduction | 49 | 42 | 28 | 61 |
| 7.5% sorbitol | 1.8 | 1.1 | 4.6 | 6.6 |
| Control | 2.9 | 1.2 | 9.6 | 8.8 |
| % Reduction | 38 | 8 | 52 | 25 |
| 10% sorbitol | 1.1 | 2.6 | 3.3 | 2.9 |
| Control | 3.6 | 3.3 | 9.6 | 8.4 |
| % Reduction | 69 | 21 | 66 | 65 |

EXAMPLE 6

The efficacy of the present invention is also demonstrated by the results of experiments showing that the tomato plants treated with the current formulations grow better after transplanted in the field. The tomato plants were treated with aqueous solutions of various concentrations of sorbitol at the ages of seven and ten days old from the sowing date. The heights of the tomato plants were measured prior to the transplanting and seven and ten days after transplanting. The growth rates of the treated plants are compared with those of the control plants in the Tables. The growth of the tomato plants whose heights have been reduced by the application of the present invention are greater than the growth rates of the control plants, i.e. the reduced tomato plants are catching up to the control plants in height. The plants treated with 7% and 10% solutions appeared to be excessively stunted and the growth rates of the plants were not completely recovered yet.

TABLE 5

Growth Development of Tomato Plants After Transplanting

| Treatment | Plant Height (cm) | | | | Growth Rate (mm/day) | |
|---|---|---|---|---|---|---|
| | Age of Treatment (days) | | | | | |
| | 7 | | 10 | | 7 | 10 |
| % sorbitol | Age of Measurement (days) | | | | | |
| | 48 | 56 | 50 | 59 | 48–56 | 50–59 |
| Control | 40.6 | 48.7 | 34.2 | 41.1 | 10.1 | 7.7 |
| 0.5% | 43.0 | 50.6 | 35.9 | 43.0 | 9.5 | 7.9 |
| 1.0% | 39.8 | 48.3 | 35.7 | 42.8 | 10.6 | 8.9 |
| 1.5% | 39.5 | 46.8 | 33.8 | 41.3 | 9.1 | 8.3 |
| 2.0% | 41.1 | 48.3 | 33.9 | 41.1 | 9.0 | 8.0 |
| 2.5% | 34.1 | 43.6 | 33.6 | 41.3 | 11.9 | 8.5 |
| 3.0% | 34.6 | 43.4 | 30.4 | 37.9 | 11.0 | 8.3 |
| 4.0% | 30.4 | 40.8 | 30.1 | 38.1 | 13.0 | 8.9 |
| 5.5% | 31.1 | 39.8 | 22.3 | 32.0 | 10.9 | 10.8 |
| 7.0% | 30.2 | 37.9 | 26.5 | 33.9 | 9.6 | 8.2 |
| 8.0% | 27.8 | 34.7 | 25.0 | 33.7 | 8.6 | 9.7 |
| $LSD_{0.05}$ | 0.35 | 4.01 | 2.91 | 4.05 | | |

Number of plants per treatment was 6.

EXAMPLE 7

The procedure of Example 6 was repeated. The tomato plants (15 days old from the sowing date) were root drenched with aqueous solutions of various concentrations of sorbitol. The height reduction of tomato plants treated three times with a 1% solution is greater than the height reduction of tomato plants treated once with a 3% solution. Although the duration of the effectiveness is extended due to the repeated application, repeated application with a low concentration is a more effective way of reducing plant heights than a single application of high concentration.

TABLE 6

Growth Rates of Tomato Plants Treated With Single and Repeated Root Drenches of Sorbitol

| Period(days) | Growth rate per day (mm/day) | | | |
|---|---|---|---|---|
| Treatment | 1% | 2% | 3% | 5% |
| 0–4 | 2.21 | 2.19 | 2.43 | 1.85 |
| Treatment | 2 × 1% | 2 × 2% | 3% | 5% |
| 0–8 | 2.71 | 2.27 | 3.56 | 2.37 |
| Treatment | 3 × 1% | 3 × 2% | 3% | 5% |
| 0–10 | 2.53 | 1.91 | 3.61 | 2.69 |
| 0–12 | 4.05 | 2.91 | 5.93 | 4.85 |
| 0–14 | 2.91 | 1.95 | 4.12 | 3.83 |
| 0–16 | 3.20 | 2.54 | 4.12 | 3.68 |

*The second application was made 4 days after the first application and the third was 8 days after the first.

EXAMPLE 8

The efficacy of the present invention is also demonstrated by experiments showing that the plants conditioned with the present invention are hardier against drought stress. A set of four tomato plants per each treatment including control was transplanted to 4 inch (in diameter) pot 29 days after the last treatment. After uniform soil water conditions were established, watering was stopped for a week.

The tomato plants conditioned 31 days prior to the water denial remained turgid and have dark green leaves while unconditioned plants (control plants) are severely wilted.

This long-lasting conditioning effect has been confirmed by an outside university evaluation. A set of 22 week old and plug-grown seedlings was treated with two sequential applications of an aqueous solution of 1% sorbitol. The treated plants exhibited a very rapid growth inhibition relative to the control plants. The difference was apparent within several days. After an additional two weeks, the plants in the plugs were transplanted into 6 inch standard pots to evaluate seedling response to water stress. After soil water conditions were established, water was withheld and plants were observed daily to evaluate the effects of the present invention. After ten days without water, the difference between treated and control seedlings was remarkable and distinct. Untreated plants were severely wilted, while treated plants remained turgid and had dark green leaves. There was no lasting growth inhibition, however, and the differences in leaf turgor do not appear to be related to differences in plant size.

EXAMPLE 9

The effectiveness of the present invention in hardening plants against chilling and freezing stress is demonstrated by experiments showing that tomato plants treated with an aqueous solution of 5% sorbitol are tolerant to low temperature. Ten day old (from the germination date) tomato seedlings were treated with an aqueous solution of 5% sorbitol (15 ml for two seedlings). An equal number of plants were treated with DI water for control. Seven days after treatment, the plants were exposed to freezing temperatures. The following results were observed.

| Control: | Fully developed leaves | Injured at −2° C. after one-half hour exposure |
|---|---|---|
| | Young expanding leaves | Injured at −3° C. after one hour exposure |
| Treated: | Fully developed leaves | Injured at −2° C. after one-half hour exposure |
| | Young expanding leaves | Injured at −4 to −5° C. after one hour exposure. |

The tomato plants were transplanted from the seedling tray 20 days after the treatment. Ten days after the transplanting, the plants were moved to an environmental growth chamber and were exposed to chilling conditions. The temperature of the growth chamber was set to 4° C. for night and 25° C. for day. The leaves of the control plants had burned tips and were wilted after three days exposure to the chilling conditions, while no injury signs were observed on the leaves of the treated plants. Although the plants were exposed to the chilling conditions 30 days after the treatment, the tomato plants conditioned by the present invention were hardier against chilling stress.

EXAMPLE 10

Four different cultivars of tomato plants were root drenched with aqueous solutions of sorbitol, xylitol and water. The growth rates and plant heights were measured 0, 4, and 6 days after the treatments as listed in Table 7. The growth rates of all four different cultivars were reduced significantly with 3 and 5% treatments of either sorbitol or xylitol. The degree of reduction in growth rates with xylitol treatment is compatible with the degree of reduction with sorbitol treatment. The plants treated with low concentrations (0.5 and 1%) is not showing significant changes in growth rates and plant heights as compared with the control plants treated with water only.

TABLE 7

Plant Heights(cm) of Four Different Cultivars of Tomato Plants Treated with Sorbitol, Xylitol and DI Water.

| Treatment/ Measurement Age (days) | No. of Plants Tested | Xylitol | | | | | | | | Sorbitol | | | | | | | | LSD.05 |
|---|---|---|---|---|---|---|---|---|---|---|---|---|---|---|---|---|---|---|
| | | 0.5% | Water | 1% | Water | 3% | Water | 5% | Water | 0.5% | Water | 1% | Water | 3% | Water | 5% | Water | |
| *Beefsteak Tomato* | | | | | | | | | | | | | | | | | | |
| 14/14 | 40 | | | | | 4.37 | 4.53 | 4.28 | 4.74 | | | | | | | 4.54 | 4.55 | 0.62 |
| 14/18 | 40 | | | | | 5.99 | 8.24 | 4.99 | 8.30 | | | | | | | 4.60 | 8.04 | 0.81 |
| Growth rate(mm/d) | | | | | | 4.1 | 9.3 | 1.8 | 8.9 | | | | | | | 0.2 | 8.7 | |
| 18/18 | 10 | 8.04 | 7.02 | 9.26 | 9.01 | 8.24 | 7.23 | 9.25 | 8.86 | 6.82 | 7.63 | 8.00 | 8.89 | 8.25 | 6.97 | 8.07 | 8.00 | 0.80 |
| 18/24 | 10 | 18.98 | 19.20 | 20.82 | 23.28 | 16.43 | 19.26 | 15.66 | 19.92 | 15.59 | 19.30 | 15.70 | 19.73 | 13.45 | 18.06 | 9.30 | 17.38 | 1.88 |
| Growth rate(mm/d) | | 18.2 | 20.3 | 19.3 | 23.7 | 13.7 | 20.1 | 10.7 | 18.4 | 14.6 | 19.5 | 12.8 | 18.1 | 8.7 | 18.5 | 2.1 | 15.6 | |
| *Lemonboy Tomato* | | | | | | | | | | | | | | | | | | |
| 14/14 | 40 | | | | | 4.02 | 4.09 | 4.12 | 3.68 | | | | | | | 3.90 | 3.79 | 0.47 |
| 14/18 | 40 | | | | | 5.73 | 7.88 | 4.72 | 7.25 | | | | | | | 3.94 | 7.78 | 0.74 |
| Growth rate(mm/d) | | | | | | 4.3 | 9.5 | 1.5 | 8.9 | | | | | | | 0.1 | 10.0 | |
| 18/18 | 10 | 6.96 | 7.97 | 7.33 | 7.45 | 7.46 | 8.02 | 6.52 | 7.45 | 7.27 | 7.45 | 7.32 | 7.40 | 7.83 | 8.18 | 7.55 | 7.25 | 0.59 |
| 18/24 | 10 | 14.00 | 15.74 | 14.85 | 16.95 | 12.61 | 16.11 | 10.02 | 15.44 | 15.59 | 17.19 | 13.71 | 17.54 | 12.23 | 16.74 | 8.87 | 15.52 | 1.21 |
| Growth rate(mm/d) | | 11.7 | 13.0 | 12.5 | 15.8 | 8.6 | 13.5 | 5.8 | 13.3 | 13.9 | 16.2 | 10.7 | 16.9 | 7.3 | 14.3 | 2.2 | 13.8 | |
| *Betterboy Tomato* | | | | | | | | | | | | | | | | | | |
| 14/14 | 40 | | | | | 3.71 | 3.69 | 3.67 | 3.62 | | | | | | | 3.61 | 3.65 | 0.57 |
| 14/18 | 40 | | | | | 5.50 | 6.88 | 4.68 | 7.05 | | | | | | | 3.88 | 6.96 | 0.78 |
| Growth rate(mm/d) | | | | | | 4.5 | 8.0 | 2.5 | 8.6 | | | | | | | 0.7 | 8.3 | |
| 18/18 | 10 | 5.67 | 6.31 | 6.12 | 6.95 | 5.53 | 5.67 | 6.30 | 5.76 | 6.37 | 5.46 | 7.93 | 7.00 | 5.98 | 7.30 | 4.67 | 6.96 | 0.77 |
| 18/24 | 10 | 15.57 | 16.28 | 16.47 | 18.65 | 11.47 | 20.34 | 10.66 | 16.81 | 17.34 | 17.66 | 17.16 | 20.57 | 9.41 | 20.80 | 6.36 | 19.71 | 2.24 |
| Growth rate(mm/d) | | 16.5 | 16.6 | 17.3 | 19.5 | 9.9 | 24.7 | 7.3 | 18.4 | 18.3 | 20.3 | 15. | 22.6 | 5.7 | 22.5 | 2.8 | 21.3 | |
| *Sunny Florida Tomato* | | | | | | | | | | | | | | | | | | |
| 11/11 | 40 | | | | | 3.69 | 3.48 | 3.64 | 3.48 | | | | | | | 3.52 | 3.48 | 0.29 |
| 11/18 | 40 | | | | | 4.26 | 5.96 | 4.74 | 5.96 | | | | | | | 5.03 | 5.96 | 0.42 |
| Growth rate(mm/d) | | | | | | 0.8 | 3.5 | 1.6 | 3.5 | | | | | | | 2.2 | 3.5 | |
| 16/16 | 50 | | | 5.23 | 5.05 | 5.12 | 4.91 | 5.13 | 5.24 | | | 5.12 | 5.39 | 5.67 | 5.45 | 5.28 | 5.24 | 0.64 |
| 16/22 | 50 | | | 9.11 | 9.30 | 8.07 | 9.50 | 7.50 | 9.13 | | | 10.03 | 9.99 | 9.82 | 10.34 | 8.68 | 9.80 | 1.22 |
| Growth rate(mm/d) | | | | 6.5 | 7.1 | 4.9 | 7.7 | 4.0 | 6.5 | | | 8.2 | 7.7 | 6.9 | 8.2 | 5.7 | 7.6 | |

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for reducing plant growth, comprising applying to the root zone of the plant a growth reducingly effective amount of a growth reducing composition consisting essentially of polyols of the formula $$CH_2OH(CHOH)_nCH_2OH,$$

where n=0 to 4.

2. The method of claim 1 in which said applying comprises applying an aqueous solution of the growth reducing composition.

3. The method of claim 2 in which the aqueous solution contains between 0.05 and 25 weight percent of the growth reducing composition.

4. The method of claim 3 in which the aqueous solution contains between 0.1 to 10 weight percent of the plant growth reducing composition.

5. The method of claim 2 in which the growth reducing composition consists essentially of an aqueous solution of sorbitol or xylitol, or a mixture thereof.

6. The method in claim 5 in which the aqueous solution contains between 0.1 to 10 weight percent of the sorbitol, xylitol or mixture thereof.

7. The method of claim 2 in which the aqueous solution further contains a non-ionic surfactant.

8. The method of claim 7 in which the aqueous solution contains between 0.005 to 0.5 weight percent of the non-ionic surfactant.

9. The method of claim 7 in which the non-ionic surfactant is selected from the group consisting of polyoxyethylene sorbitan monolaurate, polyoxyethylene sorbitan and polysiloxane.

10. A method for conditioning a plant for hardiness against damage by exposure to environmental or handling stress, which method comprises applying to the root zone of the plant a stress conditioningly effective amount of a composition consisting essentially of polyols of the formula $$CH_2OH(CHOH)_nCH_2OH,$$

where n=0 to 4.

11. The method of claim 10 in which said applying comprises applying an aqueous solution of the plant conditioning composition, wherein the aqueous solution contains between 0.05 and 25 weight percent of the plant conditioning composition.

12. The method of claim 11 in which the aqueous solution contains between 0.1 to 10 weight percent of the plant conditioning composition.

13. The method of claim 10 in which the plant conditioning composition is applied at least about one day prior to exposure of the plant to the stress.

14. The method of claim 10 in which the plant conditioning composition consists essentially of an aqueous solution of sorbitol or xylitol, or a mixture thereof.

15. The method of claim 1 in which said applying comprises root drenching, drip irrigating or direct soaking of the roots.

16. The method of claim 10 in which said applying comprises root drenching, drip irrigating or direct soaking of the roots.

* * * * *